United States Patent
Hosokawa et al.

(10) Patent No.: US 8,796,031 B2
(45) Date of Patent: Aug. 5, 2014

(54) MICROCHIP FOR PLATELET EXAMINATION AND PLATELET EXAMINATION DEVICE USING SAME

(75) Inventors: Kazuya Hosokawa, Tokyo (JP); Tomoko Wada, Tokyo (JP); Masashi Fukasawa, Tokyo (JP); Taro Kondo, Tokyo (JP); Maki Terada, Tokyo (JP)

(73) Assignee: Fujimori Kogyo Co., Ltd. (JP)

( * ) Notice: Subject to any disclaimer, the term of this patent is extended or adjusted under 35 U.S.C. 154(b) by 22 days.

(21) Appl. No.: 13/578,019

(22) PCT Filed: Feb. 10, 2011

(86) PCT No.: PCT/JP2011/052901
§ 371 (c)(1),
(2), (4) Date: Aug. 9, 2012

(87) PCT Pub. No.: WO2011/099569
PCT Pub. Date: Aug. 18, 2011

(65) Prior Publication Data
US 2012/0301966 A1 Nov. 29, 2012

(30) Foreign Application Priority Data
Feb. 10, 2010 (JP) ................. 2010-028090

(51) Int. Cl.
*G01N 33/86* (2006.01)
*G01N 33/48* (2006.01)
*G01N 11/04* (2006.01)
*G01N 11/08* (2006.01)
*G01N 33/543* (2006.01)
*G01N 33/49* (2006.01)

(52) U.S. Cl.
CPC ...... *G01N 33/4905* (2013.01); *G01N 2800/222* (2013.01); *G01N 33/54393* (2013.01)
USPC ............... 436/69; 436/63; 436/148; 436/180; 422/73; 422/82.13; 422/502; 422/503; 422/504; 422/505; 422/554; 435/2; 435/29

(58) Field of Classification Search
USPC ..................... 436/63, 69, 148, 174, 177, 180; 422/68.1, 73, 82.13, 501, 502, 503, 422/504, 505, 513, 534, 547, 551, 554; 435/2, 29
See application file for complete search history.

(56) References Cited

U.S. PATENT DOCUMENTS 5,290,692 A 3/1994 Suzuki et al.
5,888,826 A 3/1999 Ostgaard et al.
(Continued)

FOREIGN PATENT DOCUMENTS

EP 1950567 A1 7/2008
JP 11506215 6/1999
(Continued)

OTHER PUBLICATIONS

International Patent Application No. PCT/JP2011/052901, International Search Report mailed Mar. 15, 2011 (2 pages).
(Continued)

*Primary Examiner* — Maureen Wallenhorst
(74) *Attorney, Agent, or Firm* — Kilpatrick Townsend & Stockton LLP (57) ABSTRACT

A microchip for measuring platelet function by allowing blood to flow through a channel to induce platelet aggregation, wherein the microchip has a channel provided inside thereof, wherein at least a part of the channel is coated with collagen for allowing adhesion of platelets; a plurality of walls extend along the direction of the flow of blood in the channel and divide the width of the channel to form a channel dividing section; and the walls are treated to have a surface roughness (Ra) of 10 to 200 nm.

17 Claims, 6 Drawing Sheets

(56) References Cited

U.S. PATENT DOCUMENTS

| | | | |
|---|---|---|---|
| 7,005,857 | B2 | 2/2006 | Stiene et al. |
| 7,091,048 | B2 | 8/2006 | Parce et al. |
| 8,372,342 | B2 | 2/2013 | Hosokawa |
| 8,425,840 | B2 * | 4/2013 | Hosokawa et al. ........... 422/68.1 |
| 2006/0034734 | A1 * | 2/2006 | Schubert et al. .............. 422/101 |
| 2007/0092399 | A1 | 4/2007 | Yokomine |
| 2007/0254325 | A1 | 11/2007 | Rechner |
| 2009/0068668 | A1 | 3/2009 | Duer |
| 2009/0311675 | A1 | 12/2009 | Hosokawa |
| 2010/0267066 | A1 | 10/2010 | Hosokawa et al. |
| 2011/0151500 | A1 * | 6/2011 | Hosokawa et al. ............. 435/29 |
| 2012/0058500 | A1 * | 3/2012 | Mitchell et al. ................. 435/13 |

FOREIGN PATENT DOCUMENTS

| | | |
|---|---|---|
| JP | 2001252897 | 9/2001 |
| JP | 2002277479 | 9/2002 |
| JP | 2002528703 | 9/2002 |
| JP | 2004004002 A | 1/2004 |
| JP | 2004251630 | 9/2004 |
| JP | 2004257766 A | 9/2004 |
| JP | 2005034129 A | 2/2005 |
| JP | 2006501449 | 1/2006 |
| JP | 2006145345 A | 6/2006 |
| JP | 2006205080 | 8/2006 |
| JP | 2007024522 | 2/2007 |
| JP | 2007147602 A | 6/2007 |
| JP | 2007271323 A | 10/2007 |
| JP | 2007298511 A | 11/2007 |
| JP | 2009068874 A | 4/2009 |
| JP | 2009223142 A | 10/2009 |
| WO | 9734698 A1 | 9/1997 |
| WO | 9800231 A1 | 1/1998 |
| WO | 0023802 A1 | 4/2000 |
| WO | 2004029221 A2 | 4/2004 |
| WO | 2006037321 A1 | 4/2006 |
| WO | 2007046450 | 4/2007 |
| WO | 2007132481 | 11/2007 |
| WO | 2009069656 A1 | 6/2009 |
| WO | 2010/018833 * | 2/2010 |

OTHER PUBLICATIONS

U.S. Appl. No. 12/744,500, "Office Action", mailed Jul. 5, 2012.
PCT Application No. PCT/JP2008071445, Supplemental Search Report, Jun. 7, 2011.
Grabowski, "Platelet Aggregation in Flowing Blood at a Site of Injury to an Endothelial Cell Monolayer: Quantitation and Real-Time Imaging with the TAB Monoclonal Antibody", Blood, Jan. 15, 1990, vol. 75, No. 2; 390-398.
Tsuji et al., "Real-Time Analysis of Mural Thrombus Formation in Various Platelet Aggregation Disorders: Distinct Shear-Dependent Roles of Platelet Receptors and Adhesive Proteins Under Flow", Blood, Aug. 1, 1999, vol. 94, No. 3; 968-975.
Notice of Allowance mailed Dec. 26, 2012 in U.S. Appl. No. 12/744,500, 10 pages.
International Preliminary Report on Patentability mailed Sep. 27, 2012 in PCT Application No. PCT/JP2011/052901.
Satoh, Kaneo, et al., "Platelet Aggregability Test," Thrombosis and Circulation, 2004, pp. 17-20, vol. 12, No. 4. *Concise explanation of relevance is submitted in concurrently filed "Supplemental Information Disclosure Statement".*
Takahashi, Shinichi, et al., "Measurement of Platelet Aggregability with PFA-100," Thrombosis and Circulation, 2005, pp. 90-94, vol. 13, No. 3. *Concise explanation of relevance is submitted in concurrently filed "Supplemental Information Disclosure Statement".*
International Patent Application No. PCT/JP2009/064202, International Search Report mailed Dec. 8, 2009, 2 pages.
U.S. Appl. No. 13/058,612, Non-Final Office Action mailed May 3, 2013, 10 pages.
European Patent Application No. 09806724.2, Supplementary European Search Report mailed Jul. 8, 2013, 7 pages.
Russian Patent Application No. 201110901115, Official Action mailed Jul. 10, 2013, 8 pages.
U.S. Appl. No. 13/058,612, Response to Non-Final Office Action filed Aug. 5, 2013, 15 pages.
Japanese Patent Application No. 2010-524736, Office Action mailed Aug. 6, 2013, 8 pages.
U.S. Appl. No. 13/058,612, Final Office Action mailed Aug. 28, 2013, 8 pages.
U.S. Appl. No. 13/058,612, Response to Final Office Action filed Nov. 29, 2013, 16 pages.
U.S. Appl. No. 13/058,612, Advisory Action mailed Dec. 6, 2013, 2 pages.
U.S. Appl. No. 13/058,612, Amendment and Response to Advisory Action and Request for Continued Examination filed Dec. 30, 2013, 16 pages.

* cited by examiner

MICROCHIP FOR PLATELET EXAMINATION AND PLATELET EXAMINATION DEVICE USING SAME

PRIOR RELATED APPLICATIONS

The present application is a national phase of PCT/JP2011/052901, filed Feb. 10, 2011, which claims the benefit of priority to Japanese Patent Application No. 2010-028090, filed Feb. 10, 2010, each of which is incorporated herein by reference in its entirety.

TECHNICAL FIELD

The present invention relates to a microchip for investigating platelet function of blood using a small amount of the blood, and a testing device using it.

BACKGROUND ART (Problems in Prior Art of Platelet Aggregation Test)

Activation and aggregation of platelets play a central role in thrombus formation (white thrombus) in the artery and primary hemostasis.

Platelets directly and indirectly bind to collagen existing under vascular endothelial cells when a blood vessel is damaged. Under an environment with slow blood flow (under low shear stress), the platelets mainly bind to collagen directly via collagen receptors such as GPVI, while under an environment with fast blood flow (under high shear stress), vWF binds to collagen and GPIbα receptors of platelets bind to vWF, causing indirect binding of the platelets to the collagen. Direct and indirect interactions with collagen activate platelets, and by such stimulation, various platelet-activating substances such as ADP and serotonin are released from dense granules and α-granules.

Those released platelet-activating factors activate their own platelets and platelets around them. In activated platelets, fibrinogen receptors GPIIb and IIIa are structurally changed to activated forms, changing the platelets to the high-affinity form for fibrinogen. Through dimeric fibrinogen, the activated platelets are continuously cross-linked to each other to form platelet aggregates.

However, most conventional aggregometers employ a method based on measuring of the processes of activation and aggregation of platelets caused by stimulation with a large amount of a platelet-activating reagent (Non-patent Document 1).

Therefore, the platelet activation reaction is induced under an environment very different from physiological platelet activation conditions, and, although it is possible to measure evident differences in functions such as congenital dysfunction of receptors, it is difficult to measure platelet functions in a condition more similar to a physiological environment.

PFA-100 (Platelet Function Analyzer: Non-patent Document 2) is based on a system to measure obstruction of holes caused by the overall activation of platelets due to contact with immobilized collagen, shear stress and contact with platelet-inducing substances. Therefore, this system works under an environment more similar to the physiological environment, compared with the conventional platelet aggregation by stimulation with a single platelet-activation induction substance. However, it has been impossible to control variation of data and the concentrations of induction substances contained in the blood to be allowed to pass through the holes. Therefore, platelet aggregation induced under conditions in which platelet-activation induction substances are present at very low concentrations or absent, which is observed in patients whose platelets are already activated by development of thrombosis; and platelet aggregability caused by stimulation with a platelet-inducing substance at a very high concentration in cases of measurement of platelet function in patients suffering from platelet dysfunction; could not be appropriately measured.

Further, Patent Document 1 discloses a method for measuring platelet function, which comprises allowing blood to pass through the inside of a capillary and then through an opening section of a partitioning member and measuring the length of time required for obstruction of the opening section by thrombus formation at the opening section of the partitioning member. However, since, in this method, a large amount of a platelet-activating reagent is added, it is difficult to measure a detailed platelet function reflecting a physiological condition, for example, a condition where platelets are activated but reduced by addition on of high amount of a platelet activating agent, or where the number of platelets is normal but platelet function is weak.

PRIOR ART DOCUMENTS

Patent Document

Patent Document 1: JP 2007-298511A

Non-Patent Documents

Non-patent Document 1: Platelet Aggregability Test, Thrombosis and Circulation, vol. 12, No. 4, pp. 17-20, 2004
Non-patent Document 2: Measurement of Platelet Aggregability with PFA-100, Thrombosis and Circulation, vol. 13, No. 3, pp. 90-94, 2005

SUMMARY OF THE INVENTION

For example, in diseases such as sepsis and disseminated intravascular coagulation syndrome (DIC), platelets are in an activated state due to vascular endothelial disorder and thrombus formation, and complexes between platelets and leukocytes or the like are also formed. Further, because of extreme consumption of platelets due to continuous thrombus formation, a bleeding symptom may also occur in spite of the thrombus formation in the body.

In conventional platelet function tests, it has been difficult to carry out an assay which strictly reflects such symptom.

For example, in the turbidimetric method, when the reactivity against a platelet-inducing substance is promoted, platelet function is judged to be promoted (strong) even in cases where the number of platelet is reduced. Further, since complexes between platelets and leukocytes, which are formed by inflammatory response or the like in the body, and largely affect thrombus formation, precipitate together with erythrocytes during centrifugation for preparation of platelet-rich plasma, and therefore, these are not contained in platelet-rich plasma.

Further, since, in cases where PFA-100 is used, the concentration of the induction substance employed for measurement is the same between patients having strong platelet function and patients having weak platelet function, it is impossible to appropriately carry out a test to confirm natural aggregation induction which occurs under conditions where the induction substance is absent or present at a very low concentration, or to confirm, in a patient to whom an antiplatelet agent was administered, the pharmacological effect of the agent under conditions where the concentration of the induction substance is very high. Further, even in cases where the obstruction delayed in measurement with PFA-100, it is difficult to carry out, for example, data comparison between a case where platelet function is weak and a case where the number of platelets is small while platelet function is promoted (activated in the body).

The present invention was accomplished in view of the above-described circumstances, and aims to provide a device and a method which enable efficient and accurate evaluation of platelet function under an environment equivalent to the blood flow by using a small amount of blood.

To solve the problems, the present invention provides a microchip for measuring platelet function by allowing blood to flow through a channel to induce platelet aggregation, which comprises a channel provided inside thereof, wherein at least a part of the channel is coated with collagen for adhesion of platelets; a plurality walls extend along the direction of the flow of the blood in the channel and divide the width of the channel to form a channel dividing section; and the walls have been treated to have a surface roughness (Ra) of 10 to 200 nm. Preferably, the channel dividing walls are placed at a position on the channel where the platelet-adhesive surface (collagen-coated section) is provided, and extend along the direction of the flow of the blood. The surface roughness of parts in the channel other than the channel dividing section is preferably less than 10 nm.

The treatment for achieving a surface roughness (Ra) of 10 to 200 nm is preferably plasma irradiation or UV irradiation.

Further, the microchip preferably has a pressure resistance to not less than 80 kPa when the inflow pressure of blood is measured while the blood is allowed to flow through the channel at a constant rate to allow formation of a platelet aggregate.

Further, the microchip preferably has an impurity inflow-preventing section provided upstream of the channel dividing section (upstream of the thrombus formation-inducing section in terms of the direction in which blood flows along the channel).

The present invention also provides a platelet function testing device comprising any of the above microchips.

The platelet function testing device preferably comprises a container for storing blood, a liquid sending pump for sending the blood from the container to the channel in the microchip, and a pressure sensor for measuring the pressure exerted on the pump.

Further, the platelet function testing device preferably comprises, downstream of the collagen-coated section inside the microchip (downstream of the collagen-coated section in terms of the direction in which blood flows along the channel), a waste liquid reservoir section for storing blood waste which has passed through the collagen-coated section.

The present invention also provides a method for testing platelet function, which comprises allowing blood to flow through the channel in any of the microchips or in any of the platelet function testing devices to cause platelet aggregation in the channel dividing section and the collagen-coated section, and measuring the inflow pressure of the blood on the channel to test platelet function.

Effect of the Invention

According to the microchip for platelet function of claim 1 of the present invention, since, in a part of the channel inside the microchip, a collagen-coated section and a channel dividing section comprising channel dividing walls extending along the direction of the flow of the blood in the channel and dividing the width of the channel, which channel dividing walls have been treated to have a surface roughness (Ra) of 10 to 200 nm, are provided, a platelet aggregate formed on the collagen is stabilized in the channel dividing section to cause stronger and more stable pressure increase, leading to improved data reproducibility. The strong increase in the pressure enables evaluation of firmness, fragility and stability (durability) of the platelet aggregate.

According to the microchip fur platelet function of claim 2 of the present invention, since the treatment for achieving a surface roughness (Ra) of 10 to 200 nm is performed by plasma irradiation or UV irradiation, not only physical properties (surface roughness) but also chemical properties (introduction of functional groups such as hydroxy, imide and amide) of the surfaces of the channel dividing walls can be made appropriate for platelet aggregation.

According to the microchip for platelet function of claim 3 of the present invention, since the surface roughness of parts other than the channel dividing section in the channel is less than 10 nm, formation of a platelet aggregate is specifically promoted in the platelet-adhesive surface (collagen-coated section) and the channel dividing section, so that the formation of the platelet aggregate can be specifically analyzed.

According to the microchip for platelet function of claim 4 of the present invention, since the pressure resistance is not less than 80 kPa when the inflow pressure of blood is measured while the blood is allowed to flow through the channel at a constant rate to allow formation of a platelet aggregate, the measurement can be performed at a higher sensitivity.

According to the microchip for platelet function of claim 5 of the present invention, since an impurity inflow-preventing section is provided upstream of the channel dividing section, measurement errors due to impurities in the sample are less likely to occur, and accurate measurement is therefore possible.

Since the platelet function testing device of claim 6 of the present invention has the microchip for platelet function according to any of claims 1 to 5 of the present invention, platelet aggregation can be efficiently promoted, and platelet function can be measured promptly at high sensitivity.

According to the platelet function testing device of claim 7 of the present invention, since the device comprises a container for storing blood, a liquid sending pump for sending the blood from the container to the channel in the microchip, and a pressure sensor for measuring the pressure exerted on the pump, platelet function can be quantitatively evaluated based on the pressure of the inflowing blood, which is preferred.

According to the platelet function testing device of claim 8 of the present invention, since the device comprises, downstream of the collagen-coated section inside the microchip, a waste liquid reservoir section for storing blood waste which has passed through the collagen-coated section, removal of blood waste by suction is not necessary, which makes the test simple.

According to the platelet function testing device of claim 9 of the present invention, since blood is allowed to flow through the channel in any of the microchips or in any of the platelet function testing devices to cause platelet aggregation in the channel dividing section and the collagen-coated section, while the inflow pressure of the blood on the channel is measured to test platelet function, platelet aggregation can be efficiently promoted and platelet function can be measured promptly at high sensitivity.

EMBODIMENTS FOR CARRYING OUT THE INVENTION

The microchip for testing platelets and the platelet testing device of the present invention are described referring to figures. However, the microchip for testing platelets and the platelet testing device of the present invention are not restricted to the embodiments below. In the present invention, 'blood' includes whole blood and platelet-rich plasma.

Figure 1:
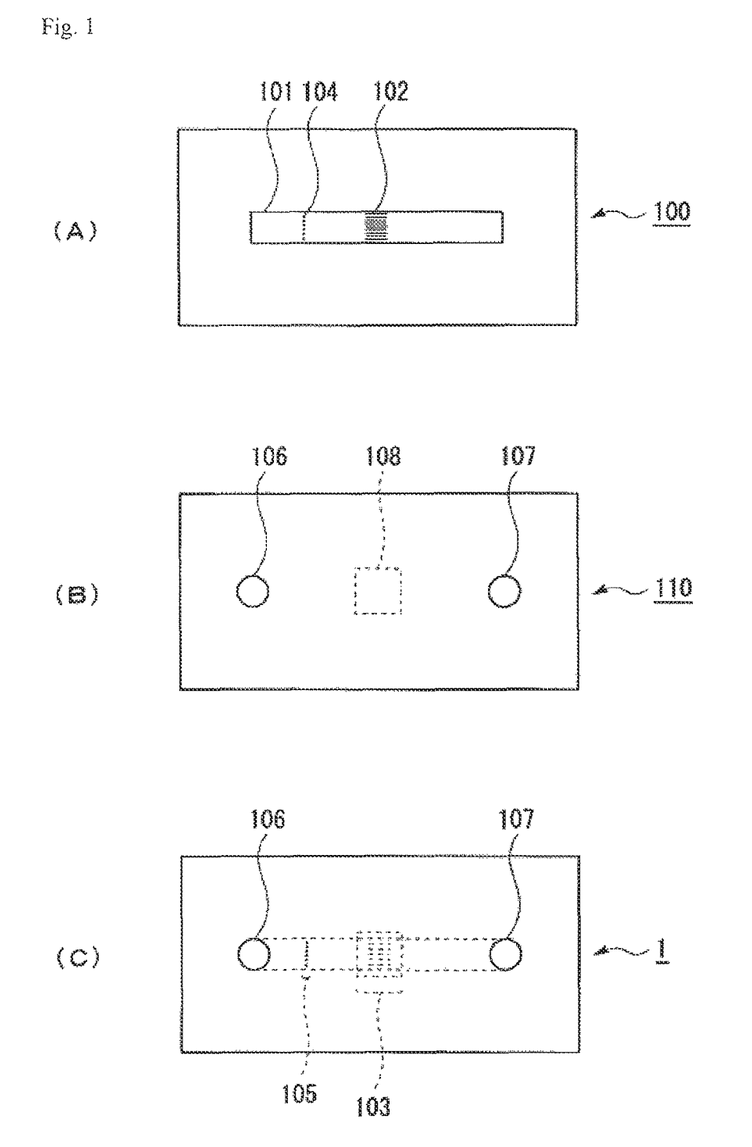
FIGS. 1A-1C show the first embodiment of the microchip for testing platelets of the present invention.

FIG. 1 is a schematic diagram showing the first embodiment of the microchip of the present invention. A description is given below based on FIG. 1.

FIG. 1(A) is a plain view showing a first substrate 100 wherein a groove corresponding to a channel 101 of a microchip 1 is engraved on the surface. The cross-sectional shape of this groove may arbitrarily be rectangular, U-shaped, V-shaped or the like. Since platelet aggregates are fragile, the depth of the groove is preferably not more than 10 to 200 μm for measuring pressure increase. The width of the groove is preferably 10 μm to 3 mm.

In a part between the first end (the end in the inlet side) and the second end (the end in the outlet side) of the groove corresponding to the channel 101, a plurality of channel dividing walls 102 extending along the direction of blood flow are provided to form a channel dividing section 103 which divides the width of the channel into a plurality of channels.

The intervals between the channel dividing walls 102 are preferably not more than 200 μm. With intervals of not more than 200 μm, when a platelet aggregate is formed, the platelet aggregate is not blown off by the blood flow even with fast blood flow and under high shear stress, and thereby can increase the internal pressure. Further, in the channel dividing section 103, the width of the channel 101 is preferably divided into not less than 5 channels by the channel dividing walls 102. That is, in cases where the width of the channel is divided into not less than 5 channels, obstruction of the respective divided channels are averaged, and therefore data with less variation can be easily obtained.

The shape of the channel dividing walls 102 is not restricted as long as they can divide the width of the channel 101 into a plurality of channels.

The channel dividing walls 102 are treated for enhancing adhesiveness of platelet aggregates such that the surface roughness (center line average surface roughness: Ra) is 10 to 200 nm. In particular, since the size of each platelet is about 1 to 2 μm, introduction of roughness with a size of 10 to 200 nm can improve adhesiveness of platelet aggregates without deteriorating the shape of the divided channel, which is preferred. This treatment is preferably performed by irradiation of plasma, UV or the like.

It is considered that adhesiveness of platelet aggregates to the channel dividing walls depends on not only physical properties (surface roughness) of the surfaces of the channel dividing walls but also chemical properties (introduction of functional groups such as hydroxy, imide and amide) of the surfaces of the channel dividing walls. It is considered that treatment by irradiation of plasma or UV not only increases the surface roughness but also introduces functional groups to the surfaces of the channel dividing walls.

Examples of the plasma treatment include atmospheric-pressure plasma, vacuum plasma and corona treatment, and examples of the UV treatment include treatments using excimer laser, mercury lamp and the like. Atmospheric-pressure plasma is especially preferred because continuous plasma treatment is possible using an inexpensive apparatus. Preferably, the plasma is specifically irradiated to the channel dividing section (channel dividing section) and promotes formation of platelet aggregates specifically on the platelet-adhesive surface (collagen-coated section) and in the channel dividing section positioned in the vicinity thereof, thereby allowing specific analysis of the formation of platelet aggregates.

When blood from a healthy individual is allowed to flow through the channel in the microchip at a constant rate to allow formation of platelet aggregates in the channel dividing section, the inflow pressure of the blood increases to about 80 kPa. Therefore, the pressure resistance of the microchip is preferably not less than 80 kPa.

In a part of the upstream of the channel dividing section 103, that is, between the channel dividing walls 102 and the first end (the end in the inlet side), a plurality of columnar bodies 104 are placed along the transverse direction of the channel at predetermined intervals, constituting an impurity inflow-preventing section 105. The intervals between the columnar bodies (length of each gap) are not restricted as long as passing of blood is allowed while passing of impurities are prevented, and the intervals are preferably 10 to 200 μm. The shape of each columnar body is not restricted, and examples of the shape include a cylinder and a polygonal column.

FIG. 1(B) is a plain view of a second substrate 110 wherein a through-hole which has an inlet 106 and an outlet 107 of the microchip 1 is provided. The positions of a penetrating hole as the inlet 106 and a penetrating hole as the outlet 107 correspond, upon lamination with the first substrate 100, to the position of the first end of the channel 101 and the position corresponding to the second end of the channel 101, respectively, on the first substrate 100. Further, a platelet-adhesive surface 108 (collagen-coated section) is formed by coating, with collagen, the position on the back side of the second substrate 110 which covers the channel dividing walls 102 on the first substrate 100 upon lamination with the first substrate 100. More particularly, as shown in FIG. 1(C), collagen is widely applied on the area that is expected to cover the channel dividing walls 102, in consideration of a safety margin.

The platelet-adhesive surface (collagen-coated section) may extend along the entire length of the channel.

FIG. 1(C) is a plain view of the microchip 1 wherein the first substrate 100 and the second substrate 110 are laminated with each other such that the groove on the first substrate 100 and the collagen-coated section of the second substrate 110 are facing inward. The wavy lines indicate that the channel 101 exists inside the microchip 1.

Figure 3:
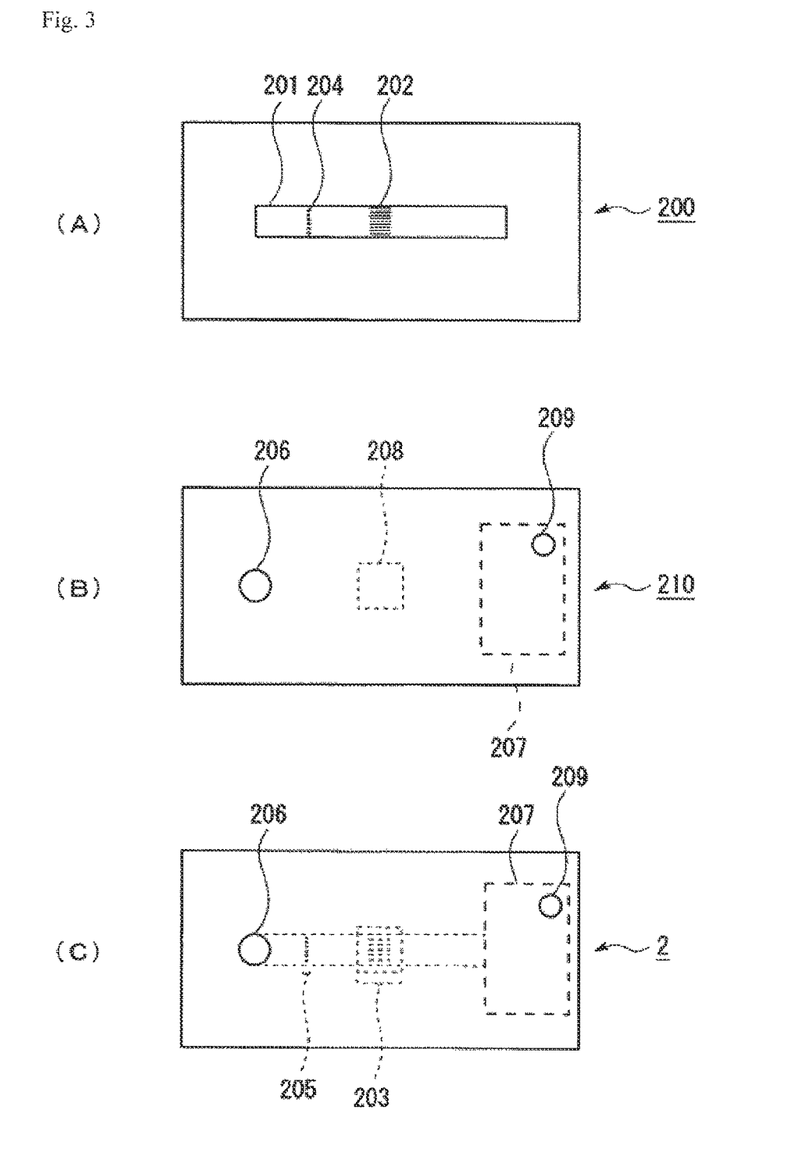
FIGS. 3A-3C show the second embodiment of the microchip for testing platelets of the present invention.

In the second embodiment of the microchip of the present invention, as shown in FIG. 3, instead of providing a penetrating hole at the position corresponding to the second end of the channel in the second substrate to provide an outlet as shown in FIG. 1, a groove connected to the position corresponding to the second end of a channel 201 may be provided in a second substrate 210 and the second substrate 210 may be attached to a first substrate 200, to provide a waste liquid reservoir section 207 for storing blood waste which has passed through a platelet-adhesive surface 208 (collagen-coated section). By setting the capacity of the waste liquid reservoir section 207 larger than the amount of the blood to be tested, discharging of blood waste by suction from the outlet with a pump or the like as in the first embodiment is not needed, and therefore, the test can be carried out more easily. A penetrating hole may be provided in the waste liquid reservoir section 207 to provide an air hole 209. By placing a blood absorbing material at the position corresponding to the penetrating hole 209 on the surface of the microchip 2, scattering of blood waste to the outside of the microchip can be suppressed even in cases where the amount of the blood sample is large. Examples of the blood absorbing material to be attached include sponges and cloths. An outlet duct may be connected to the air hole 209 for removal of the blood waste by suction.

In the microchip of the present invention, collagen coating is applied to the platelet-adhesive surface, and the coating may also comprise tissue thromboplastin in addition to collagen. In order for collagen not to be washed away from the platelet-adhesive surface by blood flow, the platelet-adhesive surface 108 or 208 is coated with collagen with high adhesive strength.

The collagen coating can be easily applied with high adhesive strength, as described in JP 05-260950 A and Blood, 1995 Apr. 1; 85(7): 1826-35, for example, by dissolving collagen into an acidic solution and applying the resulting solution to a predetermined position on a substrate such as glass or polystyrene to which hydrophilicity is given, followed by washing and drying the substrate.

In cases where a hydrophobic resin or the like is to be coated, the coating can be achieved by hydrophilizing the surface of the resin and then applying a collagen solution to a desired area, followed by air drying or drying under reduced pressure.

In cases where a plastic is used as the base material, it can be easily coated with collagen or collagen containing tissue thromboplastin by hydrophilizing its surface and then applying a collagen solution to a desired area using a dispenser such as a pipette or a syringe, followed by air drying or drying under reduced pressure.

The material of the microchip is preferably a metal, glass, plastic, silicone or the like. In view of use in blood monitoring (image analysis, especially), a transparent material is preferred. Further, in view of formation of a circuit, a plastic is preferred, and a transparent plastic is especially preferred. In cases where the material is a silicone such as PDMS (polydimethylsiloxane), substrates strongly adhere to each other, and therefore, the first substrate can be laminated with the second substrate even by pressing without using an adhesive or the like for adhesion, but in cases where a high pressure is applied to the inside of the microchip, an adhesive is preferably used. Further, it is possible to easily and effectively suppress blood coagulation at unexpected sites by using poly (2-methoxyethyl acrylate) (PMEA). The grooves and holes on the substrates of the microchip can be provided with a cutter or laser beam, and in cases where the material of the microchip is a plastic, they can also be formed by injection molding. Formation by injection molding is preferred since a microchip having a constant quality can be prepared efficiently.

An example of a platelet function test using the microchip 1 of the present embodiment will now be described based on FIG. 1(C). To the first inlet 106, a tube not shown is connected, and through the tube, a blood reservoir (blood storage section) and a liquid sending pump, which are not shown, are connected. By injecting a liquid contained in the pump from the connected pump into the reservoir, blood in the reservoir is injected into the channel of the microchip 1.

The liquid in the liquid sending pump may be a liquid having a specific gravity smaller than blood, such as mineral oil or physiological saline, and the liquid may be introduced using the liquid sending pump into the reservoir preliminarily filled with blood. The liquid may then be overlaid on the blood and pushed out by the pump, to subject the blood to be introduced into the channel. By measuring the inflow pressure of the liquid, the inflow pressure of the blood exerted on the channel can be indirectly measured. The blood with which the reservoir is preliminarily filled may also be a mixture with a platelet-activating reagent. It is also possible to place a platelet-activating reagent in the reservoir in advance in the dry or liquid state, before being mixed with the blood.

The blood is preferably subjected to anticoagulation treatment. Examples of the anticoagulant used for the anticoagulation treatment include sodium or potassium citrate; sodium or potassium oxalate; ACD (Acid Citrate Dextrose); and ethylenediaminetetraacetic acid (EDTA) salts. Such an anticoagulant may he used as a powder, freeze-dried product or solution such as an aqueous solution. Among these anticoagulants, 3.2% sodium citrate, which is commonly used, is preferred since it is easily available. In this case, it is preferred to use 1 volume of this anticoagulant with respect to 9 volumes of blood.

Examples of other anticoagulants which may be used include heparin, hirudin, thrombin aptamers and corn-derived trypsin inhibitors (1977, J. Biol. Chem, 252, 8105). More than one anticoagulant may be used. In cases where the anticoagulant employed is hirudin, stronger platelet aggregation, compared to cases of anticoagulation treatment with citric acid, occurs even without treatment with a platelet-activating reagent, and therefore, hirudin is suitable for measurement of shear stress-dependent platelet function. In the case of blood anticoagulated with citric acid, measurement of platelet function dependent on stimulation by a platelet-activating reagent can be accurately carried out, and therefore, citric acid is more suitable for evaluation of an anti-platelet agent and the like.

Examples of the method to obtain the anticoagulated blood include a method wherein the above-described anticoagulant is preliminarily added in a syringe or a vacuum blood collection tube, followed by collecting blood therewith, and a method wherein the anticoagulant is quickly added to blood immediately after collection.

It is also possible to collect blood with a vacuum blood collection tube or the like containing heparin, followed by adding heparinase and an anticoagulant suitable for the monitoring purpose, thereby degrading heparin with heparinase, to achieve replacement of heparin with the anticoagulant suitable for the measuring purpose.

In cases where the anticoagulated blood is mixed with a platelet-activating reagent, examples of the platelet-activating reagent used include ADP, collagen, thrombin, arachidonic acid and ristocetin. In such cases, evaluation of the platelet activation ability of the platelet-activating reagent can also be carried out. The platelet-activating reagent is mixed with the anticoagulated blood at a concentration at which weak platelet activation occurs. The concentration at which weak platelet activation occurs is a concentration at which irreversible platelet aggregation (secondary aggregation of platelets) does not occur under a static state. For example, in the case of ADP, it is 0.001 to 5 μM, and in the case of arachidonic acid, it is 0.001 to 1 mM. However, in cases where the reactivities to these platelet-activating reagents are clearly decreased due to abnormality of platelet function or administration of an anti-platelet agent, when measurement of the extent of the decrease is carried out, the measurement is preferably performed by adding a platelet-activating reagent at a concentration higher than the above-mentioned concentrations.

Blood which is introduced from the inlet 106 and passes through the channel 101 passes through the channel dividing section 103, and thereby shear stress is caused, and then activation of platelets is enhanced, leading to adhesion and accumulation of platelets on the platelet-adhesive surface (collagen-coated section). This causes increase in the inflow pressure of blood, and therefore, by monitoring the inflow pressure of blood, the function of platelets contained in the blood can be evaluated. Further, by monitoring the flow rate and properties of blood that passes through the channel dividing section 103, platelet function can be tested.

Impurities in the blood sample remains in the impurity inflow-preventing section 105, and do not flow into the channel dividing section 103, and therefore, the impurities do not inhibit the platelet aggregation reaction.

The blood subjected to the test is discharged from the outlet 107 provided at the end of the channel 101.

A platelet testing device of the present invention using the microchip 1 will now be described.

Figure 2:
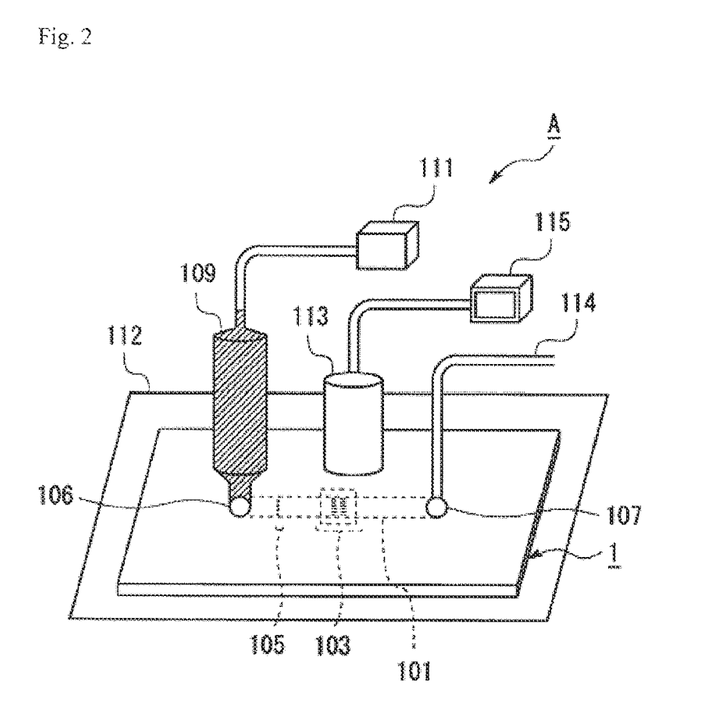
FIG. 2 shows the first embodiment of the platelet testing device of the present invention.

FIG. 2 is a view showing a frame format of a platelet testing device A as the first embodiment of the platelet testing device of the present invention, wherein the microchip 1 is constructed with transparent substrates and incorporated into the device. The first embodiment will now be described based on FIG. 2.

To the inlet 106 of the microchip 1, a reservoir 109 (blood storage section) storing anticoagulated blood is connected in an inverted position, and, to the reservoir 109, a liquid sending pump 111 for supplying mineral oil is connected. To the liquid sending pump 111, a pressure sensor not shown is connected.

From the liquid sending pump 111, mineral oil is injected into the reservoir 109, and the mineral oil is overlaid on the blood, pushing the blood into the channel 101 of the microchip 1. The blood passes through the channel 101 and reaches the channel dividing section 103 having the platelet-adhesive surface 108. On the other hand, impurities in the blood sample remains in the impurity inflow-preventing section 105.

By measuring the inflow pressure with the pressure sensor connected to the liquid sending pump 111, more quantitative platelet function test is possible. Further, by observing activation of platelets (adhesion, aggregation or the like) in the channel dividing section 103 and obstruction of the capillary caused thereby using a camera 113, platelet function can be tested. Further, also by measuring the length of time required for blood to pass through the channel 101 or the amount of blood which is passed through the channel 101, a platelet function test can be carried out.

The camera 113 is connected to an image analyzer 115, enabling imaging and the like of the state of platelet activation. The combination of visual evaluation by taking images of platelet activation inside the channel and a quantitative test for platelet activation based on pressure increase is very important in view of overall judgment of the condition of blood from a patient. For example, in cases where platelets are already activated in the body and remarkably consumed and reduced in a diseased state such as DIC, the pressure increase and the obstruction are delayed. Even in such cases, by taking images of the inside with a camera, an increase of adhesion of platelets to the platelet-adhesive surface (collagen-coated section) and an increase of aggregation of platelets can be confirmed from immediately after the beginning of the test, and therefore, overall judgment of the condition of platelets from the patient is possible. The camera 113 may be movable along the direction of blood flow in the channel 101.

Platelets may be analyzed also by fluorescent labeling with quinacrine or the like. In such cases, by monitoring a luminance per unit area based on fluorescence by image analysis, the monitoring results can be digitized, and can be obtained as data.

The microchip 1 is placed on a stage-shaped heater 112, and, by heating the microchip 1 to 37° C. with the heater 112, the monitoring can be carried out under conditions more similar to those inside the body.

The mixture containing blood which is passed through the channel dividing section 103 is smoothly discharged from the outlet 107 through an outlet duct 114.

EXAMPLES

The present invention will now be described in more detail by giving concrete Examples, but the present invention is not restricted to these Examples.

[Preparation of Microchip and Platelet Function Testing Device]

Two transparent substrates (injection-molded products manufactured by Richell Corporation) of the first substrate 100 shown in FIG. 1(A) and the second substrate 110 shown in FIG. 1(B) were prepared.

In the first substrate 100, the channel 101 had a length of 20 mm, depth of 40 μm and width of 2 mm, and, in terms of the channel dividing section 103, the channel dividing walls 102 each having a length of 1.5 mm, width of 40 μm and height of 40 μm were placed at equal intervals of 40 μm, to provide the channel dividing section 103. Further, at the position 7.5 mm distant from the first end, 13 cylinders each having a diameter of 50 μm were placed at intervals of 100 μm, to provide the impurity inflow-preventing section 105. An irradiation head of a surface modification device using atmospheric-pressure plasma irradiation PS-601SW manufactured by Wedge Co., Ltd. was placed at a height of 3.5 mm above the channel dividing section 103, and plasma irradiation treatment was carried out 4 times using a conveyor (12.5 mm/sec.); and, using a light surface treatment device PL2002N-18 manufactured by SEN LIGHTS Co., Ltd., UV irradiation was carried out with a UV lamp at a distance of 30 mm for 5 minutes.

Smoothness of the comb-shaped portion is analyzed with a non-contact profilometer NewView 6200 manufactured by Zygo Corporation in each case of untreated, after plasma-treated or after UV irradiation-treated. The results are shown in Table 1.

TABLE 1

|  | PV | Ra |
| --- | --- | --- |
| Before treatment | 20.75 | 2.62 |
| After plasma treatment | 181.21 | 35.56 |
| After UV treatment | 105.28 | 16.12 |

PV: Difference in height between the highest and lowest surfaces in an area of 0.14 × 0.105 mm (unit: nm)
Ra: Dissociation from the average height/number of measurement points (unit: nm)

The above results indicate that a surface roughness of 10 to 200 nm was achieved by either plasma treatment or UV treatment.

In the experiment below, microchips each having a plasma-treated, UV irradiation-treated or untreated channel dividing section were used.

In the second substrate 100, each of the holes corresponding to the inlet 106 and the outlet 107 was provided as a penetrating hole with an inner diameter of 2 mm and depth of 2 mm, having a cross-sectionally circular shape. Further, 0.75 mg/ml collagen type I (manufactured by Nitta Gelatin Inc.) was applied to the position in the second substrate 110 which is expected to cover the channel dividing section 103 of the first substrate 100, and the substrate was then dried under vacuum to provide the platelet-adhesive surface 108.

The side of the first substrate 100 wherein the groove corresponding to the channel 101 opens and the side of the second substrate 110 having the platelet-adhesive surface 108 were bonded together such that these face to each other, using a silane coupling agent and thermocompression bonding at 60° C. for 3 hours, to provide the microchip 1 shown in FIG. 1(C).

As shown in FIG. 2, the prepared microchip 1 was placed on a stage-shaped heater 112 (heated to 37° C.), and the reservoir 109 was connected to the inlet 106 of the microchip 1. The pump 111 was connected to the reservoir 109 via a tube, and the pressure exerted on the pump was measured with a pressure sensor which is not shown. An outlet duct 114 was connected to the outlet such that blood after the analysis can be discharged. The camera 113 to which the image analyzer 115 was connected was placed above the channel dividing section 103 of the microchip 1, thereby allowing observation of the state of platelet activation in the channel dividing section 103.

Test Examples 1 and 2, and Comparative Example 1

Blood collected from a healthy individual was subjected to anticoagulation treatment with hirudin (25 μg/ml). The anticoagulated blood was subjected to flow through a microchip whose channel dividing section was plasma-treated (Test Example 1), UV irradiation-treated (Test Example 2) or untreated (Comparative Example 1). More particularly, the reservoir 109 was filled with the anticoagulated blood, and the pump 111 was filled with mineral oil. The pump 111 was connected to the reservoir 109, and a tip of the reservoir 109 was connected to the inlet 106 of the microchip 1. By injecting mineral oil from the pump 111 at a flow rate of 18 μl/minute into the reservoir to overlay the mineral oil on the blood, the blood in the reservoir was pushed into the microchip 1 at the same flow rate, while the inflow pressure of the mineral oil (that is, the inflow pressure of the blood) was measured 3 times for each type of microchip, with a pressure sensor which is not shown.

Figure 4:
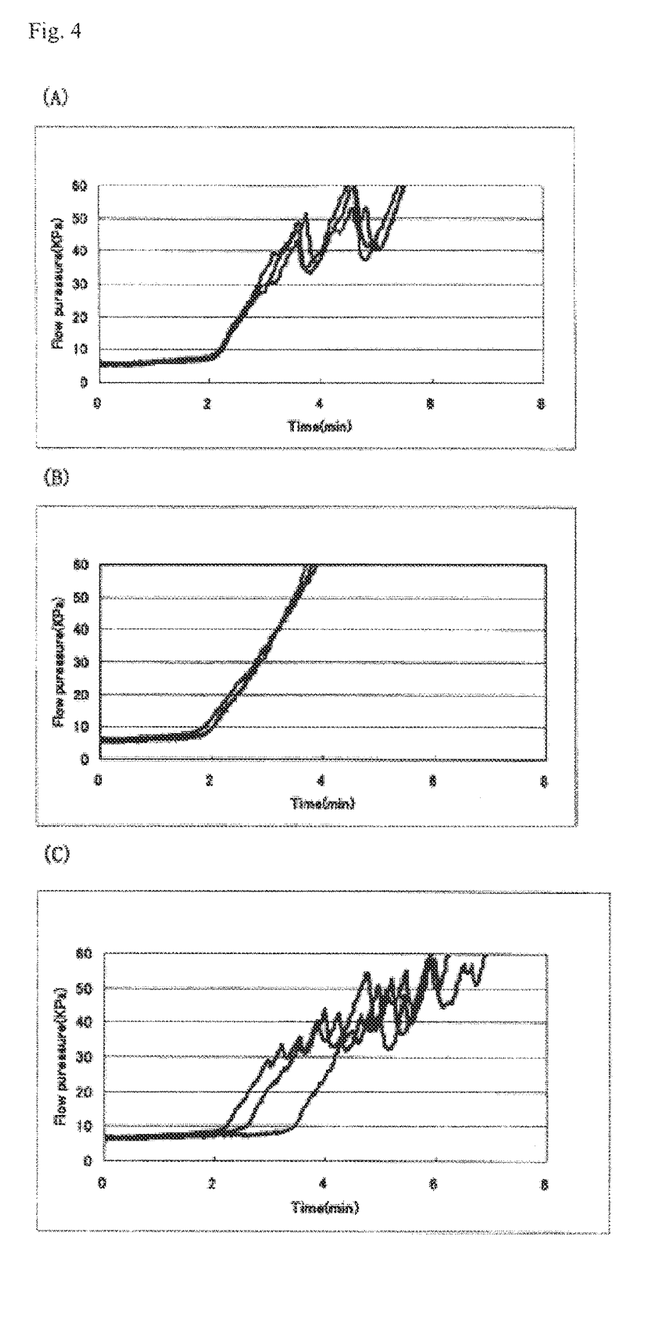
FIG. 4 is a diagram showing results of investigation of the pressure of inflowing blood using a platelet testing device having: (A) a microchip with a plasma-treated channel dividing section (Test Example 1); (B) a microchip with a UV-treated channel dividing section (Test Example 2); and (C) a microchip with an untreated channel dividing section (Comparative Example 1).

The results are shown in FIGS. 4A, 4B and 4C, respectively.

In the cases using microchip whose channel dividing section was plasma-treated (FIG. 4A) or UV-treated (FIG. 4B), more stable increase in the pressure is promoted compared to the case using the untreated microchip (FIG. 4C), and the variability in the pressure pattern was smaller in the former cases. This was assumed to be due to enhanced adhesiveness of the channel dividing section to platelet aggregates, which was achieved by the plasma treatment and the UV-irradiation treatment.

Test Example 3

Blood was collected from a sample before and after dosing of 100 mg of aspirin, and each obtained blood was subjected to anticoagulation treatment with hirudin (25 μg/ml). The anticoagulated blood was subjected to flow through the channel of a microchip having a plasma-treated channel dividing section. More particularly, the reservoir 109 was filled with anticoagulated blood (before and after dosing of 100 mg of aspirin), and the pump 111 was filled with mineral oil. The pump 111 was connected to the reservoir 109, and a tip of the reservoir 109 was connected to the inlet 106 of the microchip 1. By injecting mineral oil from the pump 111 at a flow rate of 27 μl/minute or 9 μl/minute into the reservoir to overlay the mineral oil on the blood, the blood in the reservoir was pushed into the microchip 1 at the same flow rate, while the inflow pressure of the mineral oil (that is, the inflow pressure of the blood) was measured with a pressure sensor which is not shown.

Comparative Example 2

The same operation as in Test Example 3 was carried out except that a microchip having a plasma-untreated channel dividing section was used, to measure the inflow pressure of the mineral oil.

Figure 5:
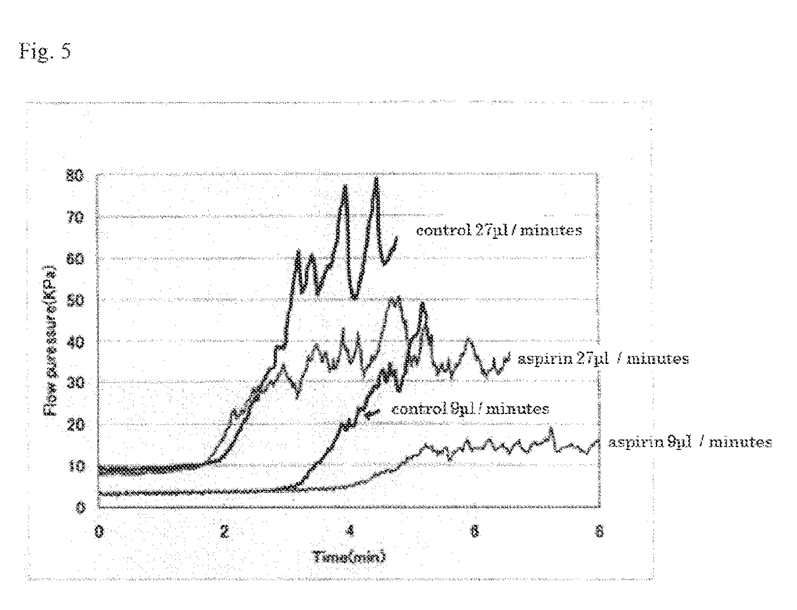
FIG. 5 is a diagram showing results of investigation of the platelet aggregation effect of aspirin using a platelet testing device having a microchip with plasma-treated channel dividing walls (Test Example 3). The ordinate represents the pressure (kPa) and the abscissa represents time (minutes). Each of blood collected from a subject to which aspirin was administered (aspirin administration) and blood collected from the same subject to which aspirin was not administered (control) are evaluated by allowing the blood to flow at a rate of 9 μl/minute or 27 μl/minute.
Figure 6:
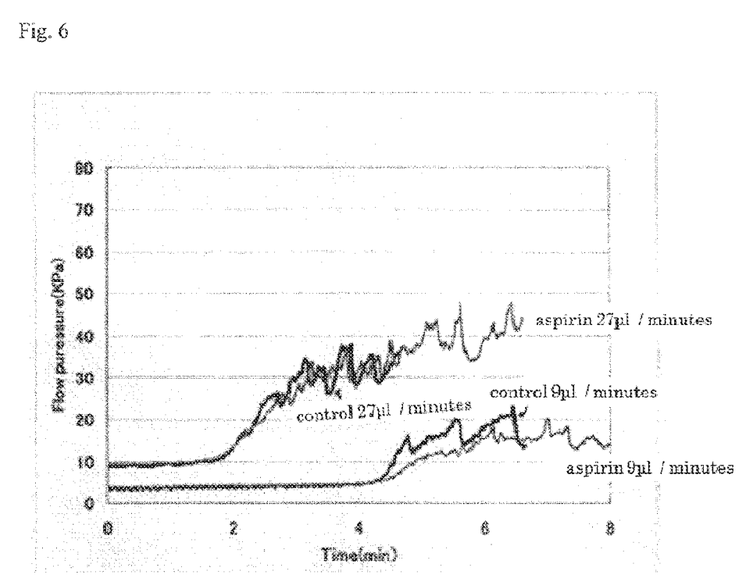
FIG. 6 is a diagram showing results of investigation of the platelet aggregation effect of aspirin using a platelet testing device having a microchip with plasma-untreated channel dividing walls (Comparative Example 2). The ordinate represents the pressure (kPa) and the abscissa represents time (minutes). Each of blood collected from a subject to which aspirin was administered (aspirin administration) and blood collected from the same subject to which aspirin was not administered (control) are evaluated by allowing the blood to flow at a rate of 9 μl/minute or 27 μl/minute.

The results of Test Example 3 and Comparative Example 2 are shown in FIGS. 5 and 6, respectively. In the case where the microchip having a plasma-untreated channel dividing section was used, the pressure increase was insufficient and the effect of aspirin could be therefore hardly identified. On the other hand, in the case where the microchip having a plasma-treated channel dividing section was used, the pressure increased to about 50 kPa at the low flow rate and to about 80 kPa at the high flow rate, which allowed sufficient identification of the effect of aspirin.

Thus, the plasma irradiation increased the pressure to a higher level, and the stability of platelet aggregates under high-flow-rate conditions could be analyzed more accurately. It can be seen that aspirin having an antiplatelet action has an effect to decrease the stability of formed platelet aggregates rather than an effect to decrease the formation rate of platelet aggregates.

Industrial Applicability

Since, by using the microchip of the present invention, platelet function of blood can be investigated with a small amount of the blood, the microchip is useful in the fields such as medical care, diagnosis, examination and research.

EXPLANATION OF LETTERS OR NUMERALS

A . . . Platelet testing device; 1, 2 . . . Microchip; 100, 200 . . . First substrate; 101, 201 . . . Channel; 102, 202 . . . Channel dividing walls; 103, 203 . . . Channel dividing section; 104, 204 . . . Columnar bodies; 105, 205 . . . Impurity inflow-preventing section; 106, 206 . . . Inlet; 107 . . . Outlet; 207 . . . Waste liquid reservoir section; 108, 208 . . . Platelet-adhesive surface (Collagen-coated section); 109 . . . Reservoir; 209 ... Air hole (outlet); 110, 210 ... Second substrate; 111 ... Pump; 112 ... Heater; 113 ... Camera; 114 ... Outlet duct; 115 ... Image analyzer.

The invention claimed is:

1. A microchip for measuring platelet function by allowing blood to flow through a channel to induce platelet aggregation, said microchip comprising:
   a channel provided inside thereof, wherein at least a part of said channel is coated with collagen for adhesion of platelets; and
   a plurality of walls that extend along a direction of flow of blood in the channel and divide the width of said channel to form a channel dividing section,
   wherein the walls have been treated to have a surface roughness (Ra) of 10 to 200 nm, and wherein said plurality of walls is placed at a position on the collagen-coated part of said channel.

2. The microchip of claim 1, wherein the treatment for achieving a surface roughness (Ra) of 10 to 200 nm is plasma irradiation or UV irradiation.

3. A method for testing platelet function, said method comprising:
   allowing blood to flow through the channel in the microchip of claim 2 to cause platelet aggregation in the channel dividing section and the collagen-coated section; and,
   measuring the inflow pressure of blood on the channel to test platelet function.

4. The microchip of claim 1, wherein the surface roughness of parts other than the channel dividing section in the channel is less than 10 nm.

5. A method for testing platelet function, said method comprising:
   allowing blood to flow through the channel in the microchip of claim 4 to cause platelet aggregation in the channel dividing section and the collagen-coated section; and,
   measuring the inflow pressure of blood on the channel to test platelet function.

6. The microchip of claim 1, wherein the microchip has a pressure resistance to not less than 80 kPa when inflow pressure of blood is measured while the blood is allowed to flow through the channel at a constant rate to allow formation of a platelet aggregate.

7. A method for testing platelet function, said method comprising:
   allowing blood to flow through the channel in the microchip of claim 6 to cause platelet aggregation in the channel dividing section and the collagen-coated section; and,
   measuring the inflow pressure of blood on the channel to test platelet function.

8. The microchip of claim 1, wherein an impurity inflow-preventing section is provided upstream of the channel dividing section.

9. A method for testing platelet function, said method comprising:
   allowing blood to flow through the channel in the microchip of claim 8 to cause platelet aggregation in the channel dividing section and the collagen-coated section; and,
   measuring the inflow pressure of blood on the channel to test platelet function.

10. A platelet function testing device comprising the microchip of claim 1.

11. The platelet function testing device of claim 10, further comprising:
    a container for storing blood;
    a liquid sending pump for sending blood from the container to the channel in the microchip; and,
    a pressure sensor for measuring the pressure exerted on the pump.

12. The platelet function testing device of claim 11, comprising a waste liquid reservoir section for storing blood waste which passes through the collagen-coated section, downstream of the collagen-coated section inside the microchip.

13. A method for testing platelet function, said method comprising:
    allowing blood to flow in the platelet function testing device of claim 11 to cause platelet aggregation in the channel dividing section and the collagen-coated section; and,
    measuring the inflow pressure of blood on the channel to test platelet function.

14. The platelet function testing device of claim 10, comprising a waste liquid reservoir section for storing blood waste which passes through the collagen-coated section, downstream of the collagen-coated section inside the microchip.

15. A method for testing platelet function, said method comprising:
    allowing blood to flow in the platelet function testing device of claim 14 to cause platelet aggregation in the channel dividing section and the collagen-coated section; and,
    measuring the inflow pressure of blood on the channel to test platelet function.

16. A method for testing platelet function, said method comprising:
    allowing blood to flow in the platelet function testing device of claim 10 to cause platelet aggregation in the channel dividing section and the collagen-coated section; and,
    measuring the inflow pressure of blood on the channel to test platelet function.

17. A method for testing platelet function, said method comprising:
    allowing blood to flow through the channel in the microchip of claim 1 to cause platelet aggregation in the channel dividing section and the collagen-coated section; and,
    measuring inflow pressure of blood on the channel to test platelet function.

\* \* \* \* \*